(12) United States Patent
Hete et al.

(10) Patent No.: US 8,298,154 B2
(45) Date of Patent: Oct. 30, 2012

(54) TECHNIQUES FOR ACCURATELY DERIVING PHYSIOLOGIC PARAMETERS OF A SUBJECT FROM PHOTOPLETHYSMOGRAPHIC MEASUREMENTS

(75) Inventors: Bernard F. Hete, Kittanning, PA (US); Eric J Ayers, Alliquippa, PA (US)

(73) Assignee: Starr Life Sciences Corporation, Oakmont, PA (US)

( * ) Notice: Subject to any disclaimer, the term of this patent is extended or adjusted under 35 U.S.C. 154(b) by 1330 days.

(21) Appl. No.: 11/972,431

(22) Filed: Jan. 10, 2008

(65) Prior Publication Data

US 2008/0167564 A1 Jul. 10, 2008

Related U.S. Application Data

(60) Provisional application No. 60/884,389, filed on Jan. 10, 2007.

(51) Int. Cl.
*A61B 5/0205* (2006.01)

(52) U.S. Cl. ........ 600/529; 600/336; 600/324; 600/508; 600/500; 600/483

(58) Field of Classification Search .................. 600/473, 600/475, 476, 477, 481, 483, 484, 500–503, 600/310, 323, 324
See application file for complete search history.

(56) References Cited

U.S. PATENT DOCUMENTS

| | | | |
|---|---|---|---|
| 2,706,927 A | 8/1949 | Wood | |
| 3,167,658 A | 7/1961 | Richter | |
| 3,094,101 A | 4/1962 | Porter | |
| 3,599,629 A | 8/1971 | Gordy | |
| 3,602,213 A | 8/1971 | Howell et al. | |
| 3,625,185 A | 12/1971 | Kester | |
| 3,638,640 A | 2/1972 | Shaw | |
| 3,704,706 A | 12/1972 | Herczfeld et al. | |
| 3,720,199 A | 3/1973 | Richton et al. | |
| 3,769,974 A | 11/1973 | Smart et al. | |
| 3,807,388 A | 4/1974 | Om et al. | |
| 3,819,276 A | 6/1974 | Kiess et al. | |
| 3,833,864 A | 9/1974 | Kiess et al. | |
| 3,847,483 A | 11/1974 | Shaw et al. | |
| 3,880,006 A | 4/1975 | Poduje | |
| 3,910,701 A | 10/1975 | Henderson et al. | |
| 3,998,550 A | 12/1976 | Konishi et al. | |

(Continued)

OTHER PUBLICATIONS

Design of Pulse Oximeters, in the Institute of Physics Publishing, Bristol Philadelphia, 1997, Edited by J.G. Webster.

(Continued)

*Primary Examiner* — Patricia Mallari
*Assistant Examiner* — Michael Catina
(74) *Attorney, Agent, or Firm* — Blynn L. Shideler; Krisanne Shideler; BLK Law Group

(57) ABSTRACT

Several techniques are disclosed for isolating either heart or breath rate data from a photoplethysmograph, which is a time domain signal such as from a pulse oximeter. The techniques involve the use of filtering in the frequency domain, after a Fast Fourier Transform (FFT) has been conducted on a given photoplethysmograph also references as a given set of discrete time-domain data. The filtering may be applied to an identified fundamental frequency and one or more harmonics for heart related parameters. The filter may be truncated to the frequency data set and further applied multiple times to improve roll off. After filtering, an Inverse FFT (IFFT) is used to reconstruct the time-domain signal, except with undesirable frequency content eliminated or reduced. Calculation or measurement of parameters is then conducted on this reconstructed time-domain signal.

23 Claims, 3 Drawing Sheets

U.S. PATENT DOCUMENTS

| | | | | |
|---|---|---|---|---|
| 4,013,067 | A | 3/1977 | Kresse et al. | |
| 4,059,991 | A | 11/1977 | Dybel et al. | |
| 4,086,915 | A | 5/1978 | Kofsky et al. | |
| 4,091,803 | A | 5/1978 | Pinda | |
| 4,167,331 | A | 9/1979 | Nielson | |
| 4,225,410 | A | 9/1980 | Pace | |
| 4,237,447 | A | 12/1980 | Clark, III | |
| 4,266,554 | A | 5/1981 | Hamaguri | |
| 4,305,401 | A | 12/1981 | Reissmueller et al. | |
| 4,350,165 | A | 9/1982 | Striese | |
| 4,370,984 | A | 2/1983 | Cartmell | |
| 4,380,240 | A | 4/1983 | Jobsis | |
| 4,406,289 | A | 9/1983 | Wesseling et al. | |
| 4,407,272 | A | 10/1983 | Yamaguchi | |
| 4,407,290 | A | 10/1983 | Wilber | |
| 4,407,298 | A | 10/1983 | Lentz et al. | |
| 4,446,715 | A | 5/1984 | Bailey | |
| 4,494,550 | A | 1/1985 | Blazek et al. | |
| 4,621,643 | A | 11/1986 | New et al. | |
| 4,700,708 | A | 10/1987 | New, Jr. et al. | |
| 4,830,014 | A | 5/1989 | Goodman et al. | |
| 5,490,523 | A | 2/1996 | Isaacson et al. | |
| 5,792,052 | A | 8/1998 | Isaacson et al. | |
| 5,797,840 | A * | 8/1998 | Akselrod et al. | 600/301 |
| 5,800,349 | A | 9/1998 | Isaacson et al. | |
| 5,927,234 | A | 7/1999 | Siegel | |
| 6,067,462 | A * | 5/2000 | Diab et al. | 600/310 |
| 6,334,065 | B1 * | 12/2001 | Al-Ali et al. | 600/323 |
| 6,446,579 | B1 | 9/2002 | Griebling | |
| 6,519,486 | B1 * | 2/2003 | Edgar et al. | 600/336 |
| 6,753,976 | B1 | 6/2004 | Torpey et al. | |
| 6,805,673 | B2 * | 10/2004 | Dekker | 600/529 |
| 2005/0004609 | A1 | 1/2005 | Stahmann et al. | |
| 2005/0065414 | A1 * | 3/2005 | Allen et al. | 600/310 |
| 2005/0209517 | A1 * | 9/2005 | Diab et al. | 600/323 |
| 2005/0276508 | A1 | 12/2005 | Coleman et al. | |
| 2006/0084877 | A1 | 4/2006 | Ujhazy et al. | |
| 2006/0122476 | A1 * | 6/2006 | Van Slyke | 600/336 |

OTHER PUBLICATIONS

Cruz et al., Laboratory Animals, 1998, vol. 32, p. 18-22.
Berkowitz, Investigative ophthalmology & Visual Science, Sep. 1996, vol. 37, No. 10, p. 2089-2098.
Sidwell et al., Antoimocrobial Agents and Chemotherapy, Feb. 1992, p. 473-476.
http://www.kentscientific.com/2002/catalogpagesearch5a.asp?page-17 Pulse Oximeter for Small Animals.

* cited by examiner

TECHNIQUES FOR ACCURATELY DERIVING PHYSIOLOGIC PARAMETERS OF A SUBJECT FROM PHOTOPLETHYSMOGRAPHIC MEASUREMENTS

RELATED APPLICATIONS

The present application claims the benefit of provisional patent application Ser. No. 60/884,389 entitled "Small Animal Pulse Oximeter Motion Artifact Rejection" filed Jan. 10, 2007.

BACKGROUND OF THE INVENTION

1. Field of the Invention

The present invention relates to medical devices and techniques for accurately deriving cardiac and breathing parameters of a subject from extra-thoracic blood flow measurements, in particular, the invention relates to medical devices and techniques for deriving breath rate, breath distention, and pulse distention measurements of a subject from a pulse oximeter system coupled to a small animal.

2. Background Information

As background, one type of non-invasive physiologic sensor is a pulse monitor, also called a photoplethysmograph, which typically incorporates an incandescent lamp or light emitting diode (LED) to trans-illuminate an area of the subject, e.g. an appendage, which contains a sufficient amount of blood. The light from the light source disperses throughout the appendage {which is broken down into non-arterial blood components, non-pulsatile arterial blood, and pulsatile blood}. A light detector, such as a photodiode, is placed on the opposite side of the appendage to record the received light. Due to the absorption of light by the appendage's tissues and blood, the intensity of light received by the photodiode is less than the intensity of light transmitted by the light source (e.g., LED). Of the light that is received, only a small portion (that effected by pulsatile arterial blood), usually only about two percent of the light received, behaves in a pulsatile fashion. The beating heart of the subject, and the breathing of the subject as discussed below, create this pulsatile behavior. The "pulsatile portion light" is the signal of interest, and effectively forms the photoplethysmograph. The absorption described above can be conceptualized as AC and DC components. The arterial vessels change in size with the beating of the heart and the breathing of the patient. The change in arterial vessel size causes the path length of light to change from $d_{min}$ to $d_{max}$. This change in path length produces the AC signal on the photo-detector, which spans the intensity range, $I_L$ to $I_H$. The AC Signal is, therefore, also known as the photoplethysmograph.

The absorption of certain wavelengths of light is also related to oxygen saturation levels of the hemoglobin in the blood transfusing the illuminated tissue. In a similar manner to the pulse monitoring, the variation in the light absorption caused by the change in oxygen saturation of the blood allows for the sensors to provide a direct measurement of arterial oxygen saturation, and when used in this context, the devices are known as oximeters. The use of such sensors for both pulse monitoring and oxygenation monitoring is known, and in such typical uses, the devices are often referred to as pulse oximeters. These devices are well known for use in humans and large mammals and are described in U.S. Pat. Nos. 4,621,643; 4,700,708 and 4,830,014, which are incorporated herein by reference.

Current commercial pulse oximeters do not have the capability to accurately measure heart rate of non-compliant subjects, particularly small mammals, or to accurately measure breath rate or other breathing related parameters in small subjects.

It is an object of the present invention to minimize the drawbacks of the existing systems and to provide medical devices and techniques for deriving accurate cardiac and breathing parameters of a subject from extra-thoracic blood flow measurements.

It is noted that, as used in this specification and the appended claims, the singular forms "a," "an," and "the" include plural referents, unless expressly and unequivocally limited to one referent. For the purposes of this specification, unless otherwise indicated, all numbers expressing any parameters used in the specification and claims are to be understood as being modified in all instances by the term "about." All numerical ranges herein include all numerical values and ranges of all numerical values within the recited numerical ranges.

The various embodiments and examples of the present invention as presented herein are understood to be illustrative of the present invention and not restrictive thereof, and are non-limiting with respect to the scope of the invention.

At least some of the above stated objects are achieved with a method of utilizing a conventional pulse oximeter signal to derive accurate heart and breath rate, particularly as applied to small mammals. At least some of the above stated objects are achieved with a method of utilizing a pulse oximeter signal to derive breath rate. As understood by those of ordinary skill in the art, a pulse oximeter is applied to the subject with a simple externally applied clip. Thus, in addition to getting oxygen saturation and heart rate from a pulse oximeter, the pulse oximeter according to the present invention can derive breath rate.

A measurement of breath rate from a pulse oximeter was first made commercially available in December 2005 by the assignee of the present application, Starr Life Sciences Corp., and is provided in the MouseOx™ device that was particularly designed for use with small mammals, namely rats and mice. In this device, the breath rate is obtained by screening out the frequency band around the heart rate point on the Fast Fourier Transform (known as FFT) that is used to identify the heart rate. The next largest amplitude to the left (or lower frequency) of the heart rate rejection band on the FFT is considered to be the breath rate. The value is then simply averaged then displayed on the screen to the user. Although useful there is room to greatly improve this calculation methodology to assure consistent, accurate results.

Pulse oximeter measurements are very susceptible to motion artifact. The reason for this sensitivity is that measurements for pulse oximetry are made at specific points in the cardiac cycle (systole and diastole). Identification of systole and diastole can only be done by observing the change in light absorption that accompanies the small peripheral blood pulse derived from the stroke volume of a cardiac cycle. One source of noise is breathing effort, which affects the blood volume delivered to the periphery in synchrony with the breathing cycle. If effort is high, the change in peripheral blood volume can be greater with breathing than with cardiac stroke volume.

A more pernicious source of noise however, is caused by motion of the tissue and sensors. Because the signal level of transmitted light is so small relative to the baseline transmitted light, very small motions of the tissue relative to the sensor pads can cause large changes in light transmission as the type and amount of tissue that resides between the LEDs and photodiode changes. If these changes happen in a rhythmic manner, it can appear to the analysis software as a cardiac stroke volume pulse, or at the very least, it can swamp the ability of the software to pick out the heart rate signal. Note that the description of these problems is identical to that which would apply to measuring breath rate.

SUMMARY OF THE INVENTION

In order to solve these problems, the present invention provides several techniques for isolating either heart or breath rate data from a photoplethysmograph. Within the meaning of this application, a photoplethysmograph is a time-domain signal such as from a pulse oximeter. The techniques of the present invention involve the use of filtering in the frequency domain, after a Fast Fourier Transform (FFT) has been conducted on a given photoplethysmograph, also referenced herein as a given set of discrete time-domain data. Several techniques are disclosed for isolating either heart or breath rate data from a photoplethysmograph, which is a time domain signal such as from a pulse oximeter. For heart-related parameters, the filtering may be applied to an identified fundamental frequency and one or more harmonics. The filter may be truncated to the frequency data set or frequency spectrum and further applied multiple times to improve roll off. After filtering, an Inverse FFT (IFFT) is used to reconstruct the time-domain signal, except with undesirable frequency content eliminated or reduced. Calculation or measurement of parameters is then conducted on this reconstructed time-domain signal.

According to one non-limiting embodiment of the invention, a method for deriving physiologic parameters of a subject from photoplethysmograph measurements comprises the steps of: A) Obtaining a frequency spectrum or data set of the time-based photoplethysmograph such as, but not limited to, the application of a Fast Fourier Transform to the time-based photoplethysmograph; B) Detecting a series of peaks of the frequency data set; C) Calculating a change of frequency between adjacent detected peaks of the series of detected peaks of the frequency spectrum; D) Identifying a repeating change of frequency between adjacent detected peaks of the series of detected peaks of the frequency spectrum; and E) Utilizing the identified repeating change of frequency to derive physiologic parameters of the subject.

The method may include the further steps of Filtering the frequency spectrum based upon the identified repeating change of frequency between adjacent detected peaks of the series of detected peaks of the frequency data set; Performing an IFFT on the filtered frequency data set to form a filtered time-based physiologic signal; and Calculating physiologic parameters from the filtered time-based physiologic signal.

The method for deriving physiologic parameters of a subject from photoplethysmograph measurements according to the invention may provide that the physiologic parameters include breathing and heart related parameters of the subject. Further the subject may be a rodent such as a mouse.

The method for deriving physiologic parameters of a subject from photoplethysmograph measurements according to the present invention may include that the step of filtering the frequency spectrum based upon the identified repeating change of frequency between adjacent detected peaks of the series of detected peaks of the frequency data set comprises the step of applying a windowed-sinc filter to the frequency data set. The windowed-sinc filter may be truncated to provide no greater number of points than is in the frequency data set to which the filter is applied. The windowed-sinc filter may be applied multiple times to the frequency data set.

The method for deriving physiologic parameters of a subject from photoplethysmograph measurements according to the present invention may provide that the step of detecting a series of peaks of the frequency spectrum or data set comprises the steps of: A) providing a preset original threshold amplitude; B) reviewing the frequency data set from high frequency to low frequency and identifying a first peak that crosses the preset original threshold amplitude value; C) setting a subsequent threshold amplitude equal to at least fifty percent of the amplitude of the last identified peak; and D) reviewing the frequency data set from high frequency to low frequency from the last identified peak and identifying a second peak that crosses the subsequent threshold amplitude value. The step of detecting a series of peaks of the frequency data set may further comprise the steps of repeating steps C) and D) to detect additional peaks.

The method for deriving physiologic parameters of a subject from photoplethysmograph measurements according to the present invention may provide that the physiologic parameters include heart rate and the detected peaks include a fundamental heart rate frequency and at least one harmonic of the fundamental heart rate frequency, and further including the steps of: Filtering the frequency spectrum to isolate the fundamental heart rate frequency and at least one harmonic of the heart rate frequency; Performing an IFFT on the filtered frequency spectrum to form a filtered time-based physiologic signal; and Calculating physiologic parameters from the filtered time-based physiologic signal. The filtering of the frequency data set may include the application of a windowed-sinc filter to the frequency data set, or a square-wave filter to the frequency data set.

One non-limiting embodiment of the present invention provides a method for deriving physiologic parameters of a subject from photoplethysmograph measurements comprising the steps of: Obtaining a frequency spectrum of the time based photoplethysmograph, such as by applying an FFT to the time based photoplethysmograph; Detecting at least one peak of the frequency spectrum or data set; Determining a fundamental frequency whereby i) if more than one peak is detected, then calculating a change of frequency between adjacent detected peaks of the series of detected peaks of the frequency spectrum and attempting to identify a repeating change of frequency between adjacent detected peaks of the series of detected peaks of the frequency data set, wherein the fundamental frequency is the repeating change of frequency, and ii) if only one peak is detected, or if a change of frequency cannot be identified, then identifying a maximum peak, wherein the maximum peak is the fundamental frequency; and Utilizing the fundamental frequency to derive physiologic parameters of the subject.

These and other advantages of the present invention will be clarified in connection with the attached figures in which like reference numerals denote like elements throughout.

DESCRIPTION OF THE PREFERRED EMBODIMENTS

Figure 1:
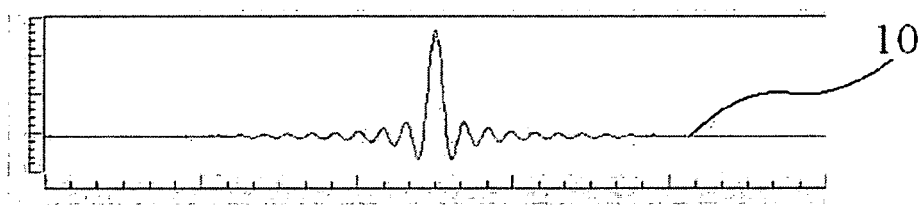
FIG. 1 is a representative illustration of a plot of a sinc function.

As described above, the present invention provides several techniques for isolating either heart or breath rate data from a photoplethysmograph, which is a time-domain signal or data set such as from known pulse oximeter sensors. A pulse oximeter system according to one aspect of the present invention is designed for small mammals such as mice and rats, such as using sensors sold under the Mouse OX™ brand by Starr Life Sciences, but the present invention is not limited to this application. The conventional pulse oximeters include a conventional light source, conventionally a pair of LED light sources, one being infrared and the other being red. The conventional pulse oximeters include a conventional receiver, typically a photo-diode. The light source and receiver are adapted to be attached to an external appendage of a subject, and may be secured to a spring-biased clip or other coupling device such as tape adhesives or the like. A specialized clip is available from Starr Life Sciences that is configured to securely attach the sensors to the tail of a subject, but any conventional clip or sensor mount could be used. The conventional sensors are also coupled to a controller and display unit, which can be a lap top computer. The use of a lap top computer as opposed to a dedicated controller and display system has advantages in the research environment.

The conventional pulse oximeters will calculate the blood oxygenation for the subject as generally known in the art of photophlysmography, and does not form the basis of the present invention. The present invention relates to techniques for obtaining improved breath rate and heart rate signals from a photoplethysmograph of the subject that is obtained from pulse oximeter sensors. Within the meaning of this application, a photoplethysmograph is a time-domain signal such as from a pulse oximeter sensor. Where the subject is a rodent, such as a mouse or rat, care must be taken to obtain accurate heart rate and oxygenation readings with conventional pulse oximeters due to the physiology of the subjects.

Square-Wave Filters for Breath Rate and Heart Rate

In the first method of the present invention, a square-wave filter is used on an FFT of the photoplethysmograph of the subject. The FFT forms what is referenced herein as a frequency data set. A square-wave filter simply involves zeroing all of the frequency data set values of the FFT result outside the region of interest, or the regions of frequencies that are intended to be retained. The desirability of a square-wave filter is that in the present application, a fairly high sampling rate can be easily used. In conjunction with a high sampling rate, a relatively small number of points are used in the FFT. The result is that the difference between two adjacent discrete frequency values on the FFT represent a very large difference in breathing or heart frequency (say on the order of 8-15 bpm). This is a small fraction of rates over 600 bpm (which is the general range of a mouse's heart rate), but when used to filter breath rate frequencies, which can be less than 100 brpm for a small rodent, the fractional error is quite large. It is obvious that the fractional error for heart rate and breath rate for human applications would be associatively larger. Additionally, the primary noise source frequency may occupy frequency bins that are very near those that represent content of the actual breath or heart rate. This situation requires extremely narrow band roll-offs of the filters.

When using traditional IIR or FIR filters, their roll-off bandwidths are extremely large, resulting in filtering that is quite insufficient for isolating frequencies of interest such that motion artifact is reduced appreciably. A square-wave on the other hand, is the narrowest filter that can be used. Such filtering does cause problems when reconstructing the time-domain signals, but in certain applications, such as the low frequencies associated with breathing, it seems to supply very nice reduction of noise without significant distortion of the time-domain breath rate signal. In this case, the filter is a band pass square-wave that is used around the breath rate.

When the square-wave is used to filter the heart rate signals, some problems do occur because of the nature of the time-domain response of a square-wave filter in the frequency domain. Thus, although a square-wave can be used to band-pass the heart rate frequency, its ability to do so while retaining true time-domain signal amplitude, something absolutely necessary to calculate the heart related Pulse Distention parameter, is quite limited.

Windowed-Sinc Filters for Breath Rate and Heart Rate

If one were to take the IFFT of a square-wave filter, the function that would appear is known as the sinc function 10, represented by the general equation $$f(x) = \frac{\sin(x)}{x}.$$

Note that this function 10 evaluated at zero would be some finite number (0/0 provides a finite result), but it turns out that the function has a value of 1 at 0. A plot of the response of this function 10 is given in FIG. 1, although it should be noted that the value of x in the function 10 form is not consistent with the abscissa labeling in the plot as the function 10 is symmetrical about x=0.

This difficulty with applying this function 10 to filtering problems is that the true function is evaluated out to ±∞. However, real data are finite, so the function 10 must be truncated. When used as a filter, this truncation causes ripple in both the stop and pass bands. To reduce the ripple, a window function is applied to the sinc function to gently roll the ends to 0, thus, the derivation of the name windowed-sinc. Any one of a number of common windows such as Hamming or Blackman can be used, or one can create his own. The windowed filter of the invention may be considered as one of a square windowed filter, a Bartlett windowed filter, a Blackman windowed filtered, a Hanning windowed filter, a Hamming window filter, and a trapezoid window filter, as all of these show certain advantages. A custom filter could also be utilized. Regarding a detailed discussion of these filters, please see "Scientist and Engineers Guide to Digital Signal Processing" by Steven W. Smith which is incorporated herein by reference. The present invention prefers to utilize the Hamming because of its superior roll-off characteristics relative to all other common windows, combined with a stop and pass band attention that is exceeded only by that of the Blackman window.

Another important property of this function when used as a filter is that the more points used in the filter function, called the kernel, the sharper its roll-off. In theory, there is no limit to the number of points that can be used to represent the function.

Lastly, the windowed-sinc filter response is symmetrical at the stop and pass endpoints. This allows its behavior to be very predictable. It can even be run more than once to effect even greater stop band attenuation that is the same number of decibels every time that it is run.

In the current approach of the present invention, the filtering is conducted in the frequency-domain, and then the time-domain signal is reconstructed using an IFFT as described above. The physiologic parameters can be then measured in the time-domain. For example, the heart rate is the period of a reconstructed time domain heart rate signal, and pulse distension is the associated amplitude. Breath rate and breath distention can be similarly measured from a reconstructed breath rate signal in the time-domain.

In the present invention, a filter kernel is utilized that has the same number of coefficients as the FFT window, or frequency data set. Although one could use smaller or larger filter kernels, kernels the same size as the frequency data set maximize the roll-off characteristic, while still making them easy to implement.

Regarding implementation, the sinc function filter kernel is a time-domain response. If applied in the time-domain, it must be convolved with the time-domain data in order to provide a filtered output. Convolution above a certain number of data points is very calculation intensive. Additionally, since we are doing an FFT of the data anyway, it is much simpler to implement the filter function in the frequency-domain. This is because convolution in the time-domain is the same as multiplication in the frequency-domain. Thus, implementation of the filter can be conducted simply by multiplying the filter kernel point by point with the FFT of the original time-domain data, since they are the same number of points. A subsequent IFFT produces the filtered time-domain output.

Figure 2:
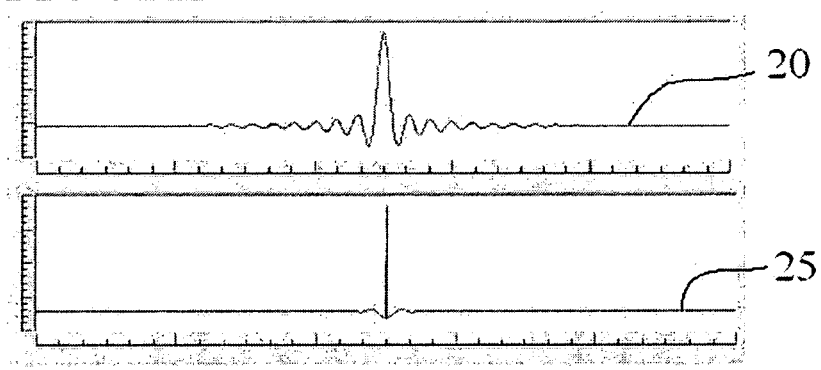
FIG. 2 is a representative illustration of a kernel for a low pass windowed sinc filter.

Windowed-sinc filters can be calculated for both low-pass and high-pass filters. In FIG. 2, an exemplary kernel for each is shown. The top kernel 20 is for a low-pass filter, and the bottom kernel 25 is for a high-pass filter.

Figure 3:
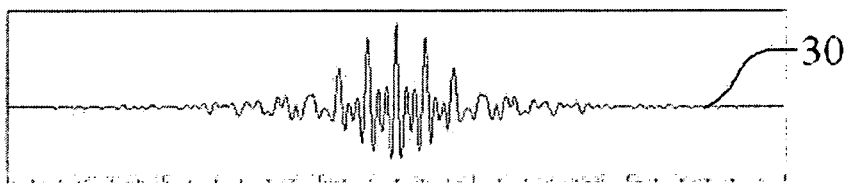
FIG. 3 is a representative illustration of a kernel for a high pass windowed sinc filter.

In addition to single filters, this method can easily implement multiple filters including multiple band-pass filters. This is done by multiplying each type of filter kernel together. A complex kernel 30 that represents 3 band-pass filters is shown in FIG. 3. Simply multiplying this kernel point by point to the FFT, then conducting an IFFT, produces the filtered time-domain signal.

This approach can be used to filter signals to isolate both heart rate and breath rate. The benefit of the windowed-sinc filter is that it does not have the large stop and pass band ripple associated with a simple square-wave filter, but it can still provide a very narrow band roll-off, which is required for our applications. It also provides the ability to adapt many low and high-pass filter kernels, such as 20 and 25, easily without significant cost in calculation time.

Multiple Passes Through The Windowed-Sinc Filter To Improve The Filter Bandwidth As stated above, the windowed-sinc filter roll-off is a function of the number of points in the filter kernel. Because the preferred version of the invention does not use more points in the filter kernel than are present in the limited size of the frequency data set resulting from the application of the FFT, inherently there is set a specific limit to the roll-off band. One method to improve the roll-off is to simply run the filter multiple times on the FFT data. The phrases "running the filter" is synonymous with "applying the filter", "applying the kernel" "passing [the data] through the filter" and other well known terms in the art. By doing multiple passes, the roll-off edge becomes steeper with each pass. For example, the frequency data amplitude at the frequency located at the midpoint of the filter roll-off (note that this frequency is defined as the cutoff frequency for windowed-sinc filters) is attenuated by 0.5. If the filter is run again, the given frequency will be attenuated by 0.25, then 0.125, and so on. There is no theoretical limit to the number of times the filter can be applied, although multiple passes will increase pass-band ripple and reduce stop-band attenuation, in the same multiplicative manner just described. As an example, if the pass band ripple has a magnitude of 1.01 at one location on a signal with a normal magnitude of 1.00, 20 multiplications (or filter passes) at this point will provide an output of 1.22, i.e. $1.01^{20}$. Additionally, time and computer round-off error will eventually impact the efficacy of this approach as well. The Hamming window has been found in this particular application to have excellent stop-band attenuation and pass-band ripple characteristics that allow more passes through the filter as compared with other windows whose characteristics are not as good.

Use of Harmonics to Identify Heart Rate in a Noisy Signal

Figure 4:
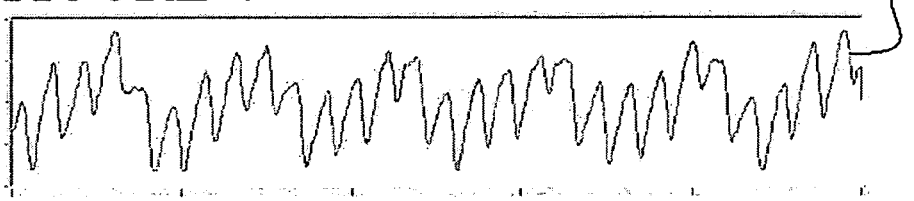
FIG. 4 is a representative illustration of a photo-plethysmograph of a subject also referenced as a raw transmitted light data of a pulse oximeter.

The techniques described above are very useful, but it is imperative to first be able to identify the heart or breath rate frequency. Knowledge of the location of either of these frequencies is necessary in order to be able to set the locations of the filter cutoffs to isolate either frequency. This is especially true if we calculate heart and breath rate using threshold crossings in the time-domain signal that results from an IFFT of signals filtered in the frequency-domain. To illustrate the difficulty of using threshold crossings without appropriate filtering, note the following sample shown in FIG. 4 of a photo-plethysmograph 40, also referenced as the raw transmitted light data or signal from a pulse oximeter, which is in the time domain. In this signal 40, the higher frequency signal represents heart rate, while the wave that the heart rate appears to ride on is the breath rate. A signal 40 like this is very difficult to analyze in the time-domain without first filtering separately for heart and breath rate.

Harmonic Heart Rate Identification Method

Figure 5:
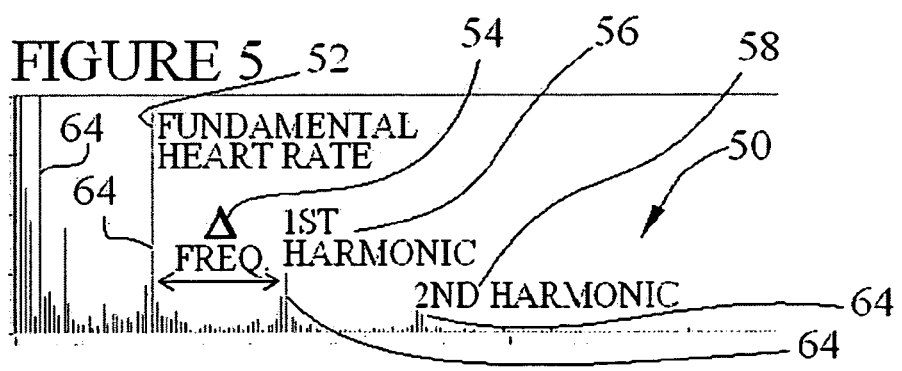
FIG. 5 is a representative illustration of a frequency-domain data set or frequency spectrum of a photoplethysmograph of a subject.

Although there are many methods for isolating heart or breath rate, the present invention has devised a method that identifies heart rate very reliably. The method makes use of two very important facets of nearly every FFT of received light data. The first is that the FFT exhibits a very low noise floor at frequencies well above the heart rate. The second is that the heart rate nearly always possesses one or more clearly identifiable harmonics. The harmonics are important in shaping the amplitude of the heart signal peaks. Thus, if one desires to accurately know the heart signal amplitude, as in the case of calculating pulse distention, it is important to retain the harmonics for signal reconstruction using the IFFT. The two characteristics described here are evident in the sample FFT or frequency data set 50 shown in FIG. 5. In this picture, the heart rate spike 52 is not the largest peak 64 on the plot, so a "largest spike is heart rate" approach does not work. Please note that peaks or spikes 64 may represent the harmonics 56, 58 or higher or the fundamental 52 or other items such as noise. There is a lot of noise/signal on the left side of the plot or data set 50, but very little on the right side. If a threshold crossing is used moving from the right side of the plot or data set 50, that is, moving from higher frequency to lower frequency, then the $2^{nd}$ harmonic 58 can be easily identified as it has significantly greater amplitude than those at the surrounding frequency bins. This is particularly evident with this spike 64 because we can see that the $2^{nd}$ harmonic 58 power is actually shared between two bins, an effect that diminishes the amplitude of both, yet the second harmonic 58 is readily apparent. In any case, it can be seen from the plot 50 that both harmonics 58 and 56 and the fundamental frequency 52 are easily identified using a threshold crossing, if it is conducted right to left, or higher frequency to lower frequency.

If one were to identify peaks 64 using a threshold crossing approaching from the right, an algorithm can be generated whereby the delta frequencies 54, or change in frequencies 54, between the spikes 64, which include the harmonics 56 and 58, can be calculated and compared. One property of harmonics 56 and 58 is that they are integral multiples of the fundamental 52. Thus, the delta frequencies 54 must be the same between the harmonics 56 and 58 and between the first harmonic 56 and the fundamental 54. Moreover, the value of the delta frequency 54 must be equal to the fundamental 52. In other words, if a repeating value of A frequency 54 can be identified out of a list of comparisons of the frequency difference between any number of detected peaks 64, the value of A frequency 54 that repeats is the fundamental heart rate 52. This value is used to set up the filtering, as the present invention anticipates that the measurements will be made in the time domain, although it is, of course, possible to make such calculations in the frequency domain.

Highly Variable Heart Rate Method

The only significant problem that can occur with this method is if the heart rate of the animal is fast and changes dramatically during a sample window the size of the FFT frequency data set. The result of such an occurrence is that the spikes 64, including harmonics 56 and 58 and higher, will be spread out. In such a case, there may be enough frequency spreading such that the fundamental 52 and harmonic heart rate spikes are diminished, and the delta method may not be viable. In such a case, the present invention resorts to a simplified method in which either a maximum peak 64 is found and labeled the heart rate, or an old (earlier calculated immediately preceding) heart rate value is used to set simple band-pass filter cutoffs. The band-pass filter is designed to cut off all low frequencies up to the heart rate, minus some tolerance band. The high end of the filter is designed to cut off frequencies, say above 30 Hz, although this limit is somewhat arbitrary and could be set at a different frequency. Also, a band-pass is not necessary, since the primary focus of this filtering is to remove breath rate and low frequency noise where motion artifact often resides.

Filter Compensation on the FFT

In the application described above, the goal is to provide a method to isolate heart rate and/or breath rate in order to reconstruct the time-domain signal without one or the other so that a simple threshold crossing technique could be used to identify that frequency. However, because the present invention is also interested in maintaining the true amplitude of the time-domain signal in order to measure breath and pulse distention, the present invention additionally may add compensation for any filtering that may have been imparted to the time-domain signal prior to its collection at this stage, which may be characterized as "pre-processing" of the signal. This can include any analog or digital filtering. This could be done at any point, but it is very simple to implement in the frequency-domain by simply characterizing the filter to be compensated, then inverting the amplitude point by point on the FFT. This can be done either discreetly, or by using a curve-fit to the filter response.

Because the heart rate signal is based on maintaining some harmonics, filter compensation may be required on a higher harmonic while lower harmonics and the fundamental may in fact be in the pass band of all of the original filters. If the goal is to retain at least two harmonics, and we have a maximum heart rate of 900 bpm (e.g., small rodents), or 15 Hz, the frequency of the second harmonic is 45 Hz. This may well be clipped by the low pass portion of the filter required for protecting the sampling system from aliasing. Thus, it might be necessary to compensate the second harmonic in this case.

Harmonic Heart Rate Identification Method with Scaled Amplitude Threshold (Increase with Decreasing Frequency)

In order to find the harmonics 56 and 58 (and higher) and the fundamental 52 using a threshold crossing approaching from the right, it is preferable to employ a method in which the threshold 62 is increased as each peak 64 is found. This is reasonable given that harmonics always exhibit some sort of logarithmic decrement from the fundamental. One approach is to simply change the threshold 62 such that it has the value related to the value of the last peak found. This approach is illustrated in frequency plot 50 of FIG. 6. As each peak 64 is found, the subsequent threshold 62 is set to a value related to the value of that peak 64 until the next peak 64 is found, at which point the threshold 62 is increased to a value related to the amplitude of that peak 64. This procedure is implemented all the way back to DC on the FFT or frequency data set. It is important to note that any number of methods scaling the amplitude for conducting threshold crossing could be used, and that this is just one example.

Figure 6:
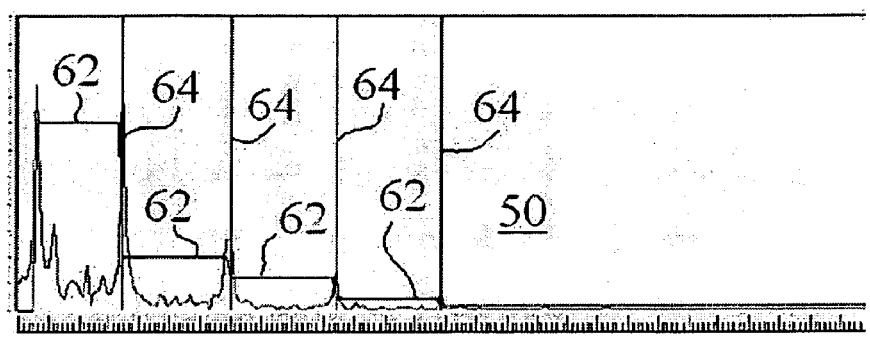
FIG. 6 is a representative illustration of a frequency spectrum of a photoplethysmograph of a subject.

The value of the threshold may be selected to be at least fifty percent (50%) of the amplitude of the last peak found, and more preferably the value of the threshold may be selected to be at least fifty percent (75%) of the amplitude of the last peak found. Further, the value of the threshold may be selected to be the amplitude of the last peak found (i.e. 100%) and it is possible to have a subsequent threshold even greater than the amplitude of the last peak found (e.g., 110% of the last peak amplitude). All of these relationships (i.e. threshold set equal to 50% of the amplitude of the last peak, threshold set equal to 75% of the amplitude of the last peak, threshold set equal to 100% of the amplitude of the last peak, and threshold set equal to 110% of the amplitude of the last peak) will result in an increasing threshold as the process is moving from right to left due to the nature of the harmonic signals. In the example of FIG. 6 the next threshold is set to 75% of the amplitude of the last peak.

Figure 7:
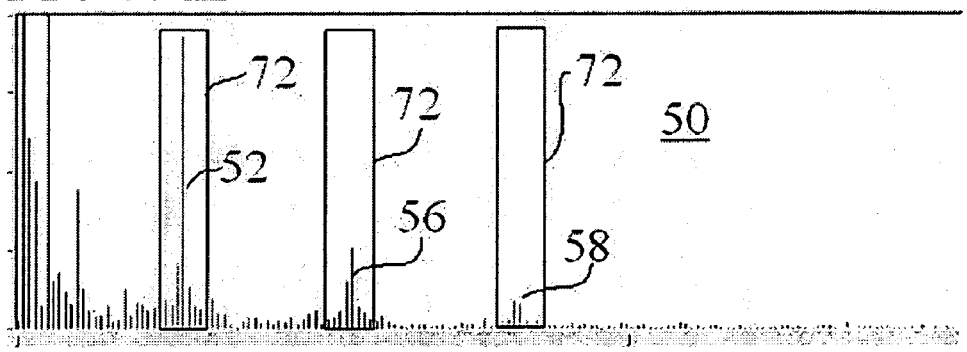
FIG. 7 is a representative illustration of a frequency domain data set or frequency spectrum of a photo-plethysmograph of a subject with filtering locations identified.
Figure 8:
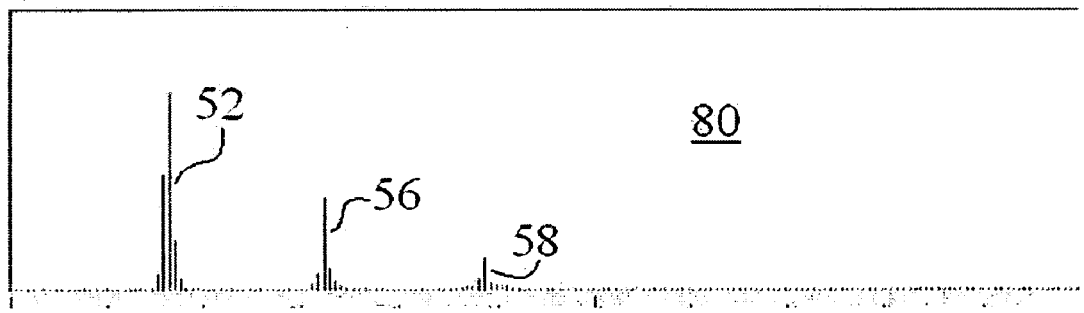
FIG. 8 is a representative illustration of a frequency-domain data set of a photo-plethysmograph of a subject that has been selectively filtered.

Use of Harmonic Heart Rate Identification for Control of Filter Ranges to Optimize Pulse Distention Recall that the goal of all of this effort is to calculate an IFFT of the original time-domain signal with only the heart rate present. The true heart rate is composed of its fundamental frequency and its harmonics. All other frequency content is noise, or frequency spreading resulting from the FFT process. In order to produce an accurate heart rate, one can employ multiple band-pass filters to save only those elements. The heart rate and its harmonics can be found using the method described above. An exemplary picture of the desired filtering is shown in FIG. 7. In this figure, the boxes 72 represent the portions of the transformed signal that we want to retain. Using the filtering methods described above, we can produce a filtered result 80 in the frequency domain as shown in the FIG. 8.

Figure 9:
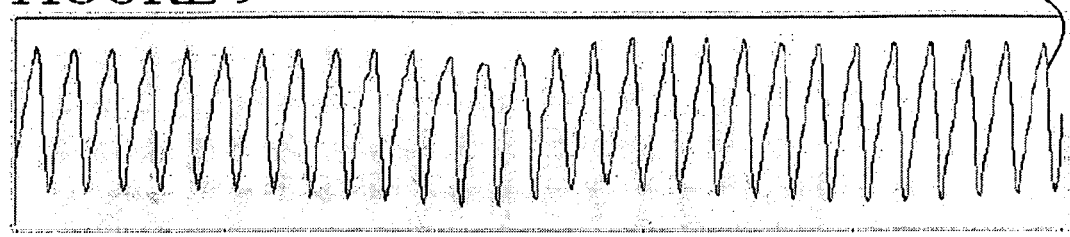
FIG. 9 is a representative illustration of a time-domain data created by taking an IFFT of a photo-plethysmograph of a subject that has been selectively filtered in the frequency domain.
Figure 10:
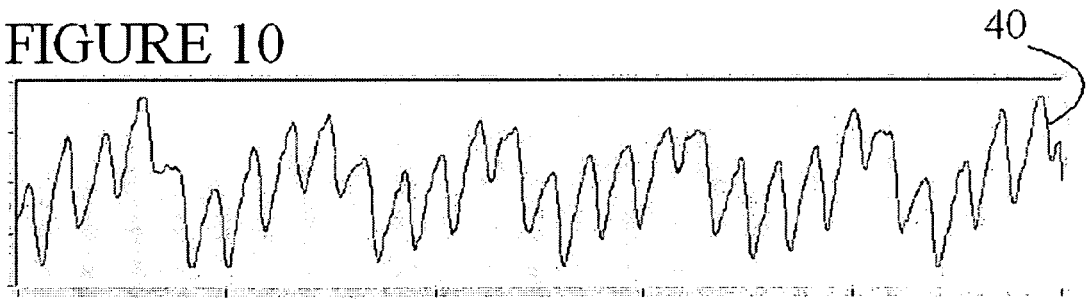
FIG. 10 is a representative illustration of a photo-plethysmograph of a subject also referenced as raw transmitted light data of a pulse oximeter, and is simply FIG. 4 repeated for the sake of comparison.

We can now take the IFFT of this frequency content 80 to obtain the filtered time domain signal 90 in the FIG. 9. This signal 90 is nearly a constant sine-wave of the heart rate. It has been filtered to remove all frequency content but the fundamental and harmonics of the heart rate signal. It has also been compensated for initial stage analog filtering. The original signal 40 is shown, for comparison in adjacent FIG. 10.

It is evident from looking at the filtered time-domain signal 90 that a threshold crossing technique in the time domain to measure heart rate would be very easy from the filtered signal 90 and very difficult in the unfiltered signal 40. Moreover, if we are interested in knowing the actual peak-to-peak amplitude for calculation of pulse distention, again it is much easier with the filtered signal 90.

As a last point, this method is illustrated on the heart rate, but we can also use such filtering techniques to cancel the heart rate signals that would allow us to get a clean breath rate signal such that we could not only accurately calculate breath rate, but also accurately calculate breath distention, a parameter that requires knowledge of the true peak-to-peak signal amplitude.

Although the present invention has been described with particularity herein, the scope of the present invention is not limited to the specific embodiment disclosed. It will be apparent to those of ordinary skill in the art that various modifications may be made to the present invention without departing from the spirit and scope thereof. The scope of the present invention is defined in the appended claims and equivalents thereto.

What is claimed is:

1. A method for deriving physiologic parameters of a subject from photoplethysmographic measurements comprising the steps of:
   Obtaining photoplethysmographic measurements from at least one light source and at least one receiver coupled to a subject;
   Obtaining a frequency spectrum of a time-based photoplethysmograph of the subject formed by at least some of the photoplethysmographic measurements;
   Implementing via a processor the steps of:
     Detecting a series of peaks of the frequency spectrum;
     Calculating a change of frequency between adjacent detected peaks of the series of detected peaks of the frequency data set; and
     Identifying a repeating change of frequency between adjacent detected peaks of the series of detected peaks of the frequency data set; and
     Utilizing the identified repeating change of frequency to derive physiologic parameters of the subject.

2. The method for deriving physiologic parameters of a subject from photoplethysmographic measurements according to claim 1 further comprising the steps of:
   Filtering the frequency spectrum based upon the identified repeating change of frequency between adjacent detected peaks of the series of detected peaks of the frequency spectrum;
   Performing an inverse fast Fourier transform (IFFTI) on the filtered frequency spectrum to form a filtered time-based physiologic signal; and
   Calculating physiologic parameters from the filtered time-based physiologic signal.

3. The method for deriving physiologic parameters of a subject from photoplethysmographic measurements according to claim 2 wherein the physiologic parameters include breathing parameters of the subject.

4. The method for deriving physiologic parameters of a subject from photoplethysmographic measurements according to claim 2 wherein the step of obtaining a frequency spectrum of a time-based photoplethysmograph of the subject is by applying a fast Fourier transform (FFT) to the time-based photoplethysmograph of the subject, and wherein the subject is a rodent.

5. The method for deriving physiologic parameters of a subject from photoplethysmographic measurements according to claim 2 wherein the step of filtering the frequency spectrum based upon the identified repeating change of frequency between adjacent detected peaks of the series of detected peaks of the frequency spectrum includes applying a windowed-sinc filter to the frequency data set.

6. The method for deriving physiologic parameters of a subject from photoplethysmographic measurements according to claim 5 wherein the windowed-sinc filter kernel has no greater number of points than are in the time-domain data set.

7. The method for deriving physiologic parameters of a subject from photoplethysmographic measurements according to claim 5 wherein the windowed-sinc filter is applied multiple times to the frequency spectrum.

8. A method for deriving physiologic parameters of a subject from photoplethysmographic measurements comprising the steps of:
   Obtaining photoplethysmographic measurements from at least one light source and at least one receiver coupled to a subject;
   Obtaining a frequency spectrum of a time-based photoplethysmograph of the subject formed by at least some of the photoplethysmographic measurements;
   Implementing via a processor the steps of:
   Detecting a series of peaks of the frequency spectrum;
   Calculating a change of frequency between adjacent detected peaks of the series of detected peaks of the frequency data set; and
   Identifying a repeating change of frequency between adjacent detected peaks of the series of detected peaks of the frequency data set; and
   Utilizing the identified repeating change of frequency to derive physiologic parameters of the subject;
   wherein the step of detecting a series of peaks of the frequency spectrum comprises the steps of:
   A) providing a preset original threshold amplitude;
   B) reviewing the frequency spectrum from high frequency to low frequency and identifying a first peak that crosses the preset original threshold amplitude value;
   C) increasing a subsequent threshold amplitude;
   D) reviewing the frequency spectrum from high frequency to low frequency from the last identified peak and identifying a subsequent peak that crosses the subsequent threshold amplitude value.

9. The method for deriving physiologic parameters of a subject from photoplethysmographic measurements according to claim 8 wherein the step of detecting a series of peaks of the frequency spectrum further comprises the steps of repeating steps C) and D) to detect additional peaks.

10. The method for deriving physiologic parameters of a subject from photoplethysmographic measurements according to claim 1 wherein the physiologic parameters include heart rate and the detected peaks include a fundamental heart rate frequency and at least one harmonic of the fundamental heart rate frequency, and further including the steps of:
   Filtering the frequency data set to isolate the fundamental heart rate frequency and at least one harmonic of the heart rate frequency;
   Performing a fast Fourier transform (IFFT) on the filtered frequency data set to form a filtered time-based physiologic signal; and
   Calculating physiologic parameters from the filtered time-based physiologic signal.

11. The method for deriving physiologic parameters of a subject from photoplethysmographic measurements according to claim 10 wherein the filtering of the frequency data set includes the application of a windowed-sinc filter to the frequency data set.

12. The method for deriving physiologic parameters of a subject from photoplethysmographic measurements according to claim 10 wherein the filtering of the frequency data set includes the application of a square window filter to the frequency spectrum.

13. The method for deriving physiologic parameters of a subject from photoplethysmographic measurements according to claim 1 further comprising the steps of filtering the frequency spectrum to compensate the frequency spectrum for an earlier applied filter.

14. A method for deriving physiologic parameters of a subject from photoplethysmographic measurements according to claim 1 further comprising the steps of:
Filtering the frequency spectrum by applying a filter to the frequency spectrum in multiple passes;
Obtaining a filtered time-based physiologic signal from the filtered frequency spectrum; and
Calculating physiologic parameters from the filtered time-based physiologic signal.

15. A method for deriving physiologic heart related parameters of a subject from photoplethysmographic measurements according to claim 1, wherein the physiologic parameters include heart rate and the detected peaks include a fundamental heart rate frequency and at least one harmonic of the fundamental heart rate frequency;
Filtering the frequency spectrum to isolate the fundamental heart rate frequency and at least one harmonic of the heart rate frequency;
Obtaining a filtered time-based physiologic heart signal from the filtered frequency spectrum; and
Calculating physiologic parameters from the filtered time-based physiologic heart signal.

16. A method for deriving physiologic parameters of a subject from photoplethysmographic measurements according to claim 1 further comprising the steps of:
Determining a fundamental frequency whereby
i) if more than one peak is detected then calculating a change of frequency between adjacent detected peaks of the series of detected peaks of the frequency spectrum and attempting to identify a repeating change of frequency between adjacent detected peaks of the series of detected peaks of the frequency spectrum, wherein the fundamental frequency is the repeating change of frequency, and
ii) if only one peak is detected or if a change of frequency cannot be identified then identifying a maximum peak, wherein the maximum peak is the fundamental frequency; and
Utilizing the fundamental frequency to derive physiologic parameters of the subject.

17. A method for deriving physiologic parameters of a subject from photoplethysmographic measurements according to claim 1 further comprising the steps of:
Filtering the frequency spectrum by applying a windowed filter on the frequency data set;
Obtaining a filtered time-based physiologic signal from the filtered frequency spectrum; and
Calculating physiologic parameters from the filtered time based physiologic signal.

18. The method for deriving physiologic parameters of a subject from photoplethysmographic measurements according to claim 17 wherein the windowed filter is a windowed-sinc filter and wherein the windowed-sinc filter kernel has no greater number of points than are in the time-domain data set.

19. The method for deriving physiologic parameters of a subject from photoplethysmographic measurements according to claim 17 wherein the windowed filter is a windowed-sinc filter and wherein the windowed-sinc filter is applied multiple times to the frequency data set.

20. The method for deriving physiologic parameters of a subject from photoplethysmographic measurements according to claim 17 wherein the windowed filter is one of a square windowed filter, a Bartlett windowed filter, a Blackman windowed filtered, a Hanning windowed filter, a Hamming window filter, and a trapezoid window filter.

21. A method for deriving physiologic parameters of a subject from photoplethysmographic measurements comprising the steps of:
Obtaining photoplethysmographic measurements from at least one light source and at least one receiver coupled to a subject;
Obtaining a frequency spectrum of a time-based photoplethysmograph of the subject formed by at least some of the photoplethysmographic measurements;
Implementing via a processor the steps of:
Detecting a series of peaks of the frequency spectrum;
Calculating a change of frequency between adjacent detected peaks of the series of detected peaks of the frequency data set; and
Identifying a repeating change of frequency between adjacent detected peaks of the series of detected peaks of the frequency data set; and
Utilizing the identified repeating change of frequency to derive physiologic parameters of the subject;
wherein the step of detecting a series of peaks of the frequency spectrum comprises the steps of
i) providing a preset original threshold amplitude;
ii) reviewing the frequency spectrum from high frequency to low frequency and identifying a first peak that crosses the preset original threshold amplitude value;
iii) increasing the subsequent threshold amplitude;
iv) reviewing the frequency data set from high frequency to low frequency from the last identified peak and identifying a second peak that crosses the subsequent threshold amplitude value; and
G) Utilizing the identified peaks to derive physiologic parameters of the subject.

22. The method for deriving physiologic parameters of a subject from photoplethysmographic measurements according to claim 21 wherein the step of detecting a series of peaks of the frequency spectrum further comprises the steps of repeating steps i) and iv) to detect additional peaks.

23. The method for deriving physiologic parameters of a subject from photoplethysmographic measurements according to claim 21 wherein the increasing of the subsequent threshold includes setting the subsequent threshold amplitude equal to at least fifty percent of the amplitude of the last identified peak.

* * * * *